(12) United States Patent
Towler

(10) Patent No.: US 10,918,471 B2
(45) Date of Patent: Feb. 16, 2021

(54) INCREASED FILM TEAR STRENGTH

(71) Applicant: W. L. GORE & ASSOCIATES, INC., Newark, DE (US)

(72) Inventor: Jeffrey C. Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/225,598

(22) Filed: Aug. 1, 2016

(65) Prior Publication Data

US 2016/0338818 A1    Nov. 24, 2016

Related U.S. Application Data

(63) Continuation of application No. 13/228,600, filed on Sep. 9, 2011, now Pat. No. 9,403,329.

(Continued)

(51) Int. Cl.
| | | |
|---|---|---|
| *A61F 2/00* | (2006.01) | |
| *B32B 38/04* | (2006.01) | |
| *A61B 17/04* | (2006.01) | |
| *A61B 17/064* | (2006.01) | |
| *A61B 46/20* | (2016.01) | |
| *B29C 55/04* | (2006.01) | |
| *B29D 7/01* | (2006.01) | |

(Continued)

(52) U.S. Cl.
CPC ........ *A61F 2/0063* (2013.01); *A61B 17/0401* (2013.01); *A61B 17/064* (2013.01); *A61B 46/20* (2016.02); *B29C 55/04* (2013.01); *B29C 65/48* (2013.01); *B29C 65/56* (2013.01); *B29C 65/62* (2013.01); *B29C 65/8215* (2013.01); *B29C 66/02242* (2013.01); *B29C 66/474* (2013.01); *B29D 7/01* (2013.01); *B32B 38/04* (2013.01); *B29C 55/12* (2013.01); *B29C 66/43* (2013.01); *B29K 2627/18* (2013.01); *B29L 2031/7532* (2013.01); *B29L 2031/7546* (2013.01); *Y10T 29/49833* (2015.01); *Y10T 29/49863* (2015.01); *Y10T 156/10* (2015.01)

(58) Field of Classification Search
CPC ....... B32B 38/04; A61F 2/0045; A61F 2/0063
USPC .................................................. 156/91, 250
See application file for complete search history.

(56) References Cited

U.S. PATENT DOCUMENTS

| | | |
|---|---|---|
| 2,671,444 A | 9/1954 | Pease, Jr. |
| 3,054,406 A | 9/1962 | Usher |

(Continued)

FOREIGN PATENT DOCUMENTS

| | | |
|---|---|---|
| EP | 352972 | 1/1990 |
| EP | 0943298 | 9/1999 |

(Continued)

OTHER PUBLICATIONS

International Search Report PCT/US2011/050931, dated Dec. 7, 2011, 3 pages.

(Continued)

*Primary Examiner* — Philip C Tucker
*Assistant Examiner* — John Blades

(57) ABSTRACT

A method of increasing the tensile strength of polymer films is provided. The creation of the load distribution elements in polymer films necessary to achieve this result is described. Application of the present invention to increase suture retention in a surgical polymer film is also provided.

22 Claims, 12 Drawing Sheets

Related U.S. Application Data

(60) Provisional application No. 61/381,286, filed on Sep. 9, 2010.

(51) Int. Cl.
   *B29C 65/48* (2006.01)
   *B29C 65/56* (2006.01)
   *B29C 65/62* (2006.01)
   *B29C 65/82* (2006.01)
   *B29C 65/00* (2006.01)
   B29L 31/00 (2006.01)
   B29C 55/12 (2006.01)
   B29K 627/18 (2006.01)

(56) References Cited

U.S. PATENT DOCUMENTS

| | | |
|---|---|---|
| 3,953,566 A | 4/1976 | Gore |
| 4,452,245 A | 5/1984 | Usher |
| 5,263,969 A | 11/1993 | Phillips |
| 5,321,109 A | 6/1994 | Bosse et al. |
| 5,358,492 A | 10/1994 | Feibus |
| 5,476,589 A | 5/1995 | Bacino |
| 5,527,341 A | 6/1996 | Gogolweski et al. |
| 5,797,932 A | 8/1998 | Min et al. |
| 5,858,505 A | 1/1999 | Moen et al. |
| 5,866,056 A | 2/1999 | Werner |
| 6,042,536 A * | 3/2000 | Tihon ............... A61B 17/0218 128/885 |
| 6,042,592 A | 3/2000 | Schmitt |
| 6,099,791 A | 8/2000 | Shannon |
| 6,165,217 A | 12/2000 | Hayes |
| 6,375,662 B1 | 4/2002 | Schmitt |
| 6,541,589 B1 | 4/2003 | Baillie |
| 6,544,167 B2 | 4/2003 | Buckberg et al. |
| 6,669,706 B2 | 12/2003 | Schmitt |
| 6,746,458 B1 | 6/2004 | Cloud |
| 7,306,729 B2 | 12/2007 | Bacino et al. |
| 7,975,698 B2 * | 7/2011 | Browning ............. A61F 2/0045 128/834 |
| 9,403,329 B2 | 8/2016 | Towler |
| 2002/0026092 A1 | 2/2002 | Buckberg et al. |
| 2004/0144395 A1 | 7/2004 | Evans et al. |
| 2006/0252980 A1 | 11/2006 | Arnal et al. |
| 2007/0112361 A1 | 5/2007 | Schonholz et al. |
| 2007/0277921 A1 | 12/2007 | Hart et al. |
| 2009/0125041 A1 | 5/2009 | Dudai |
| 2009/0216338 A1 | 8/2009 | Gingras et al. |
| 2010/0168523 A1 | 7/2010 | Ducharme |

FOREIGN PATENT DOCUMENTS

| | | |
|---|---|---|
| JP | 1975038755 B | 12/1975 |
| JP | 1987148538 | 7/1987 |
| WO | WO-1989010312 | 11/1989 |
| WO | WO-9905992 | 2/1999 |
| WO | WO-2003002027 A1 | 1/2003 |
| WO | WO-2003002027 | 9/2003 |
| WO | WO-2004017869 | 3/2004 |

OTHER PUBLICATIONS

International Search Report PCT/US2011/050958, dated Jul. 23, 2012, 5 pages.

* cited by examiner

All R_major dimensions are 0.05 inch

INCREASED FILM TEAR STRENGTH

CROSS-REFERENCE TO RELATED APPLICATIONS

This application is a continuation of U.S. application Ser. No. 13/228,600, filed Sep. 9, 2011 (issuing as U.S. Pat. No. 9,403,329 on Aug. 2, 2016), which claims the benefit of priority to U.S. Provisional Application No. 61/381,286, filed Sep. 9, 2010, which are hereby incorporated by reference in their entirety.

BACKGROUND OF THE INVENTION

Thin films are routinely used to cover or repair valuable articles. In many applications, these thin films need to be secured in place via an attachment means. Unfortunately, the increased stresses that occur at the interface between the thin film itself and the attachment means often results in premature failure under load. There are many instances where a failure occurs at the interface between the attachment means and the thin film, such as when the surgical polymer film mesh affixed to body tissue during a hernia repair, or a when panels of a filter bag are sewn together, or when a synthetic graft is used in a medical procedure. U.S. Pat. No. 5,527,341 describes a method of using additional flat membrane layers to reinforce the hole region during tendon augmentation or repair. U.S. Pat. No. 5,797,932 discusses a membrane hernia repair using a "platform-elevated part" approximately equivalent to the thickness of the base membrane. This double membrane thickness is intended to reduce tearing by the suture when after the membrane is stitched in place during the surgery.

U.S. Pat. No. 6,544,167 discusses securing a sheet material such as Dacron (Hemoshield), or polytetrafluroethylene (Gortex) to body tissue by providing a reinforcing "ring which will typically have a toroidal configuration with a circumferential cross section that is circular, and is typically formed of a plastic material or curled autogenous tissue such as fascia or pericardium, or any other biocompatible material."

US 2002/0026092 A1 discusses a reinforcing "ring can be attached to the material by adhesive or by stitches passing over the ring and through the material. Alternatively, the ring can be sandwiched between two pieces of the sheet material. In this case, a second piece of the sheet material can be positioned on the side of the ring opposite to the sheet material. Appropriate sutures extending around the ring and through the materials and will sandwich the ring and maintain it in the preferred position.

European Patent Application EP0352972A discusses the need for a thin wall expanded polytetrafluoroethylene (PTFE) "vascular graft which resists tearing by the sutures attaching it to perigraft material. [That inventive] composition comprises an expanded biocompatible fluoroplastic resin and biocompatible, high temperature-resistant fibers which are chemically compatible with the PTFE resin, wherein the fibers are distributed throughout the resin in a random orientation."

The present invention provides a method of increasing tear strength of polymer films as described herein.

SUMMARY OF THE INVENTION

An aspect of the present invention relates to a method of increasing the tear strength of polymer films. This method also can be used to increase the force necessary to pull or otherwise remove an attachment means from a polymer film to which it is affixed. This method of increasing tear strength in a polymer film is demonstrated by the inclusion of at least one load distribution element in the polymer film at a location near the foci of the applied load or attachment means. Load distribution elements such as but not limited to slits, perforations, and other apertures are included herein. Said load distribution element, serving as a stress redistribution means, increases the load required for tear propagation through or within the film. In medical articles, such as but not limited to soft tissue patches, the present invention can be used to increase suture retention and similar load bearing characteristics. Thus, this method of increasing the load carrying capability of polymer films is provided herein.

BRIEF DESCRIPTION OF THE DRAWINGS

In the figures in which like reference designations indicate like elements.

DETAILED DESCRIPTION OF THE INVENTION

The present invention provides a method of increasing tear strength in polymer films. In some embodiments, this method is suitable for polymer films to which a load is applied via an attachment point or an attachment means. The method involves the inclusion of at least one load distribution element in the polymer film at or near the foci of the applied load. This method is useful in a variety of applications including but not limited to surgical articles such as surgical polymer film meshes wherein there often is a need to increase suture retention. Thin, strong, polymer film-based, surgical polymer film meshes used to demonstrate the present invention may be useful for minimally invasive laparoscopic technique to correct vaginal prolapse, stress urinary incontinence, or similar pelvic floor disorder.

Figure 1:
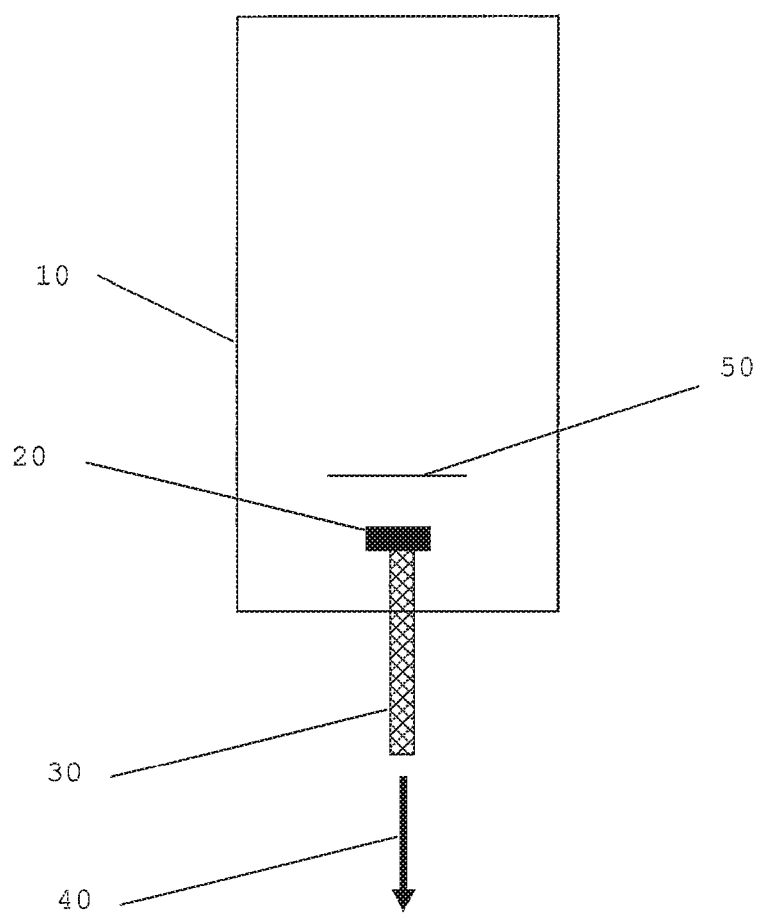
FIG. 1 is a schematic of a polymer film having a longitudinally oriented load distribution element, an attachment means, and a load source.

Polymer films suitable for the present invention include, but not limited to, those produced by either casting or extrusion and in-plane (e.g. X-Y direction) expansion. FIG. 1 depicts a flat sheet of polymer film (10) to which a tether (30) is attached via attachment means (20). When a load (40) is applied to the tether (30), the force is transferred by the tether (30) to the polymer film (10) via attachment means (20). A skilled artisan will appreciate that a range of attachment means (20) may be employed with the present invention including but not limited to adhesives, mechanical interlocking, welding, bonding, sewing, or taping. One aspect of the present invention is the inclusion of at least one load distribution element (50) which effectively increases the load required for system failure. The load distribution means (50) in this embodiment is a longitudinally oriented slit having a length greater than the width of the attachment means (20). The point of system failure is defined as the load required to cause the polymer film (10) to be substantially separated from the applied load (40). One skilled in the art will appreciate that this separation may come about by detachment of the attachment means (20), failure the polymer film (10), failure of the tether (30) or any combination thereof.

Polymer films to which the present invention applies are generally planar and have undergone in-plane expansion. These polymer films are substantially flat, thin, and flexible. They may be produced from any thermoplastic polymer or paste-extrudable polymer or castable polymer. Some typical thin films to which the present discovery applies include, but are not limited to, those made from polyolefin, polyurethane, silicone, Teflon®, or polytetrafluoroethylene (PTFE), and blends, copolymers, or composites thereof.

Polymer films suitable for the present invention are typically thin, having a thickness less than about 0.10 inch. In some embodiments, the polymer film thickness is less than about 0.050 inch. In other embodiments, the polymer film thickness is less than about 0.010 inch. And in yet other embodiments, the polymer film thickness is less than 0.002 inch thick. These polymer films are flexible and can be rolled or crumpled or folded.

A skilled artisan will appreciate that such thin polymer films are often produced from thicker films wherein the thickness is reduced by wet or dry calendaring, expansion, or both. Longitudinal, in-plane expansion (i.e. X-direction) is a common way to build strength while decreasing thickness. Subsequent inclusion of load distribution elements can further increase the longitudinal load bearing capacity of the film. The load bearing capacity of the film as described herein is defined as the tensile load required to cause specimen failure. Transverse expansion (i.e. Y-direction) may be used to build transverse strength. The inclusion of load distribution elements can further increase the transverse load bearing capacity of the film.

Some polymer films of the present discovery may comprise expanded PTFE (ePTFE) which may be produced via processes known to one skilled in the art and based on U.S. Pat. No. 3,953,566. The specific properties of the ePTFE films used herein may be tailored by the choice of PTFE resin and process conditions. In medical applications, the pore size of the resulting ePTFE film can be tailored to restrict tissue ingrowth. For many human medical applications, the ePTFE pore size should be less than the size of the cells to which it will be exposed. Typically, this requires the resulting ePTFE film to have an average pore size of 13 µm or less.

Figure 2:
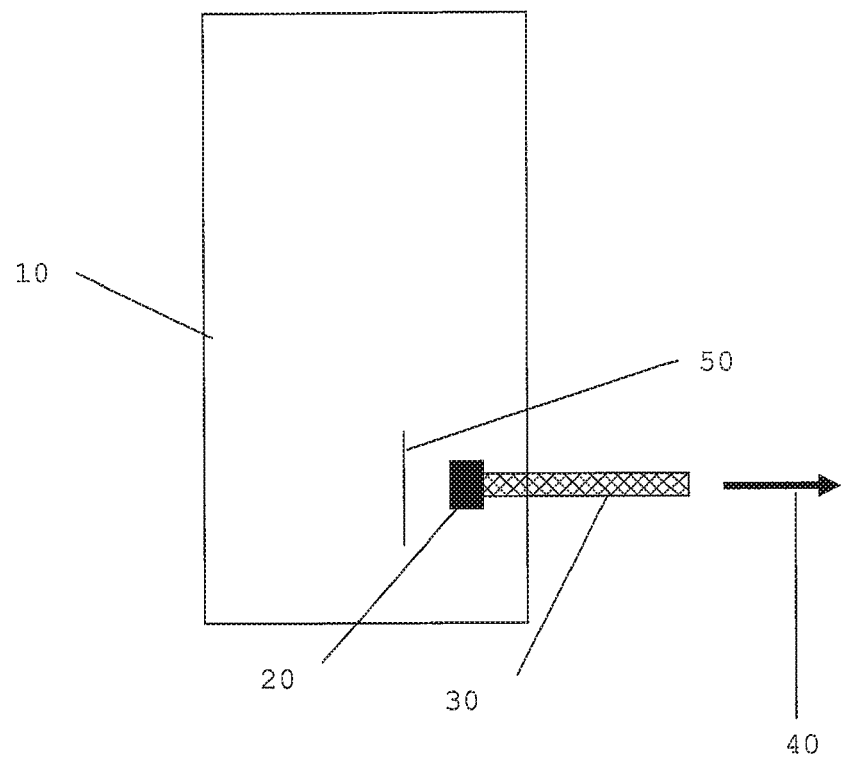
FIG. 2 is a schematic of a polymer film having a transversely oriented load distribution element, an attachment means, and a load source.

FIG. 2 depicts a bi-axially expanded polymer film (10) to which a tether (30) is attached via attachment means (20). When a longitudinally oriented load (40) is applied to the tether (30), the force is transferred from the tether (30) to the polymer film (10) via attachment means (20). The transversely oriented load distribution element (50) effectively increases the load bearing capacity of the system prior to failure. The load distribution element (50) in FIG. 2 is a slit having a width greater than the width of the attachment means (20). The point of system failure is defined as the load required to cause the polymer film (10) to be substantially separated from the applied load (40). As before, one skilled in the area will appreciate that this separation may come about by detachment of the attachment means (20), failure the polymer film (10), failure of the tether (30) or any combination of thereof.

Figure 3:
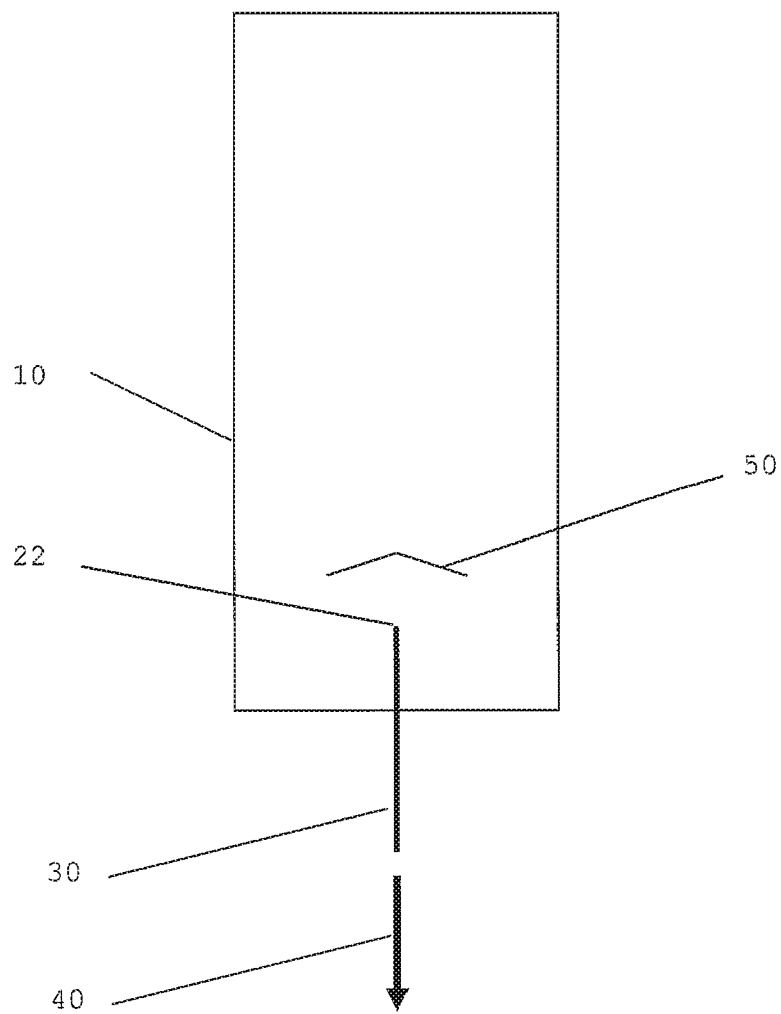
FIG. 3 is a schematic of a polymer film having a "hat" shaped load distribution element and a point load source.

FIG. 3 depicts a bi-axially expanded polymer film (10) to which a tether (30) is attached directly at location (22). When a transversely oriented load (40) is applied to the tether (30), the force is transferred from the tether (30) to the polymer film (10) at location (22). The non-orthogonal load distribution element (50) effectively increases the longitudinal load bearing capacity of the system prior to failure. The load distribution element (50) in FIG. 3 is a non-orthogonal slit having a longitudinal dimension greater than the width of the attachment at location (22) of the tether (30) to the polymer film (10). System failure is defined as the load required to cause the polymer film (10) to be substantially separated from the applied load (40). As before, one skilled in the art will appreciate that this separation may come about by failure the polymer film (10), failure of the tether (30), or a combination of thereof.

Figure 4:
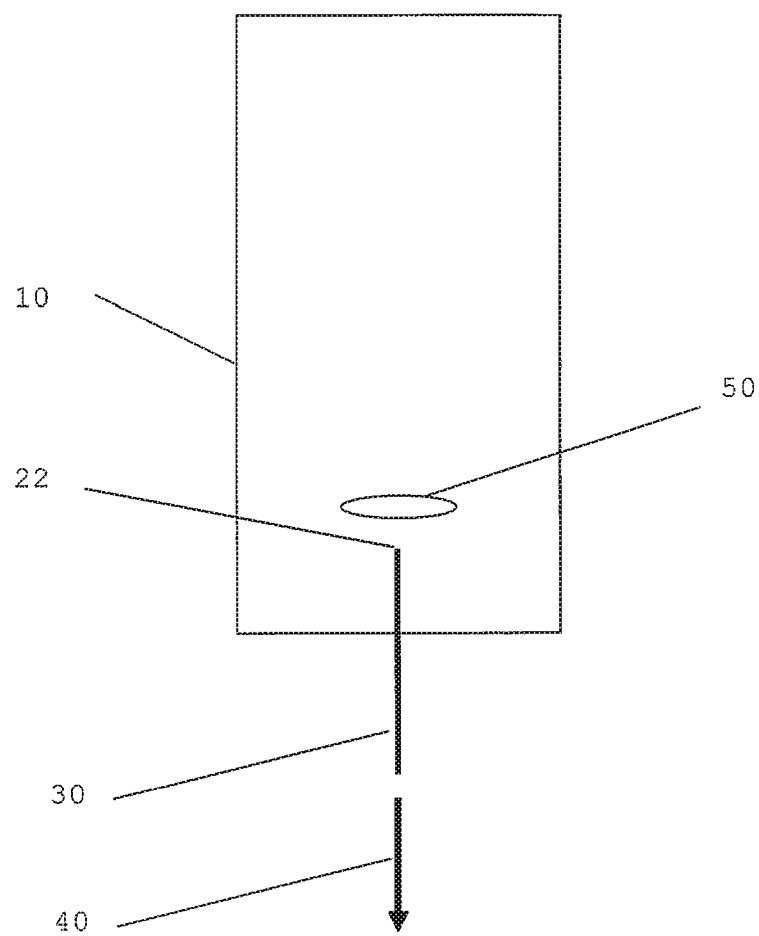
FIG. 4 is a schematic of a polymer film having an aperture load distribution element and a point load source.

FIG. 4 depicts a bi-axially expanded polymer film (10) to which a tether (30) is attached directly at location (22). When a transversely oriented load (40) is applied to the tether (30), the force is transferred from the tether (30) to the polymer film (10) at location (22). An aperture load distribution element (50) effectively increases the longitudinal load bearing capacity of the system prior to failure. The load distribution element (50) in FIG. 4 is an aperture having a longitudinal dimension greater than the width of the attachment at location (22) of the tether (30) to the polymer film (10). System failure is defined as the load required to cause the polymer film (10) to be substantially separated from the applied load (40). As before, one skilled in the art will appreciate that this separation may come about by failure the polymer film (10), failure of the tether (30), or a combination of thereof.

Figure 5:
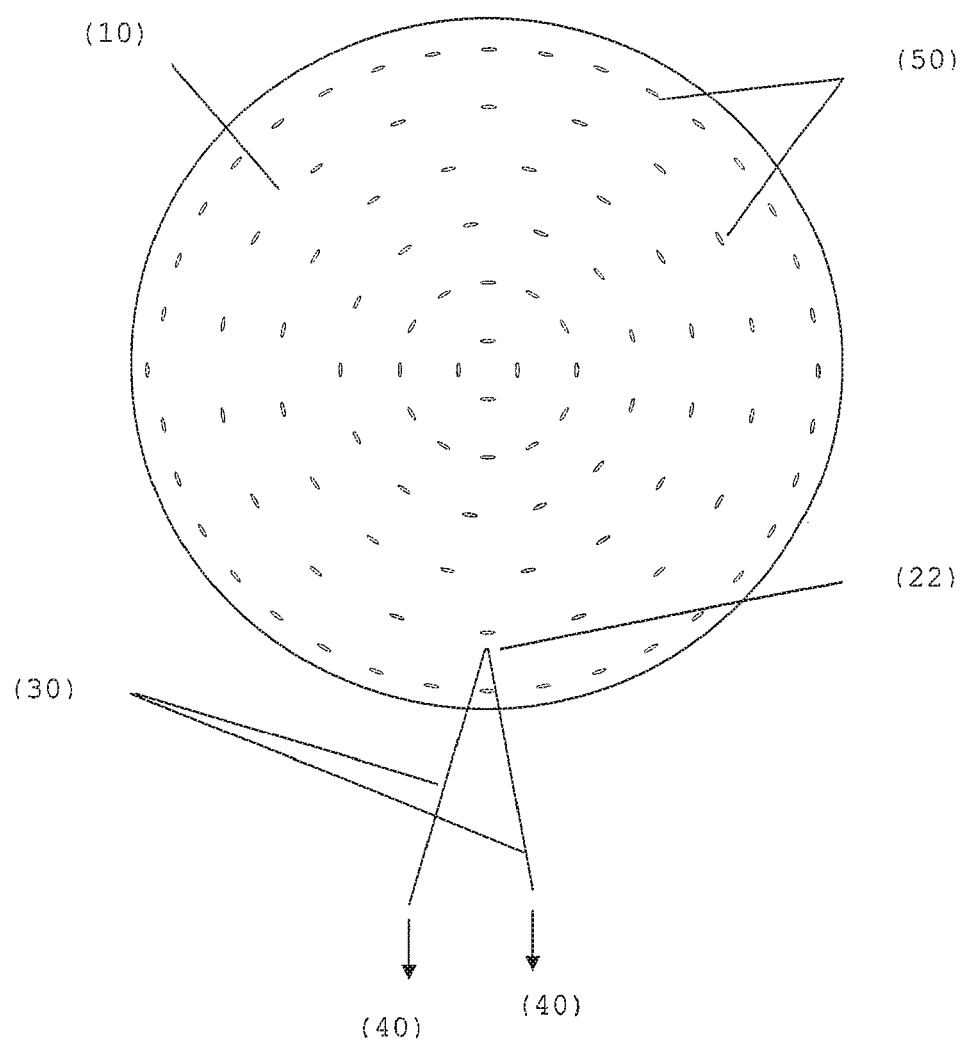
FIG. 5 is a top view of a circular polymer film having multiple load distribution elements and a load source.

FIG. 5 depicts a perforated radially expanded polymer film (10) to which a tethers (30) are attached directly at location (22). When a transversely oriented load (40) is applied to the tether (30), the force is transferred from the tether (30) to the polymer film (10) at location (22). The tether may be a string or line or rope or suture or cable or any other similar tensile element. The attachment means at location (22) may be passing the tether (30) through the polymer film (10) or affixing it to the polymer film surface. The array of circumferentially oriented load distribution elements (50) effectively increase the load bearing capacity of the system prior to failure. Load distribution elements (50) in FIG. 5 are slits. Other load distribution element types may also be used in this embodiment such as, but not limited to, cross-hatched slits, circles, ellipses, curved slits, and the like. System failure is defined as the load required to cause the polymer film (10) to be substantially separated from the applied load (40). As before, one skilled in the art will appreciate that this separation may come about by failure the polymer film (10), failure of the tether (30), or a combination of thereof.

Figure 6:
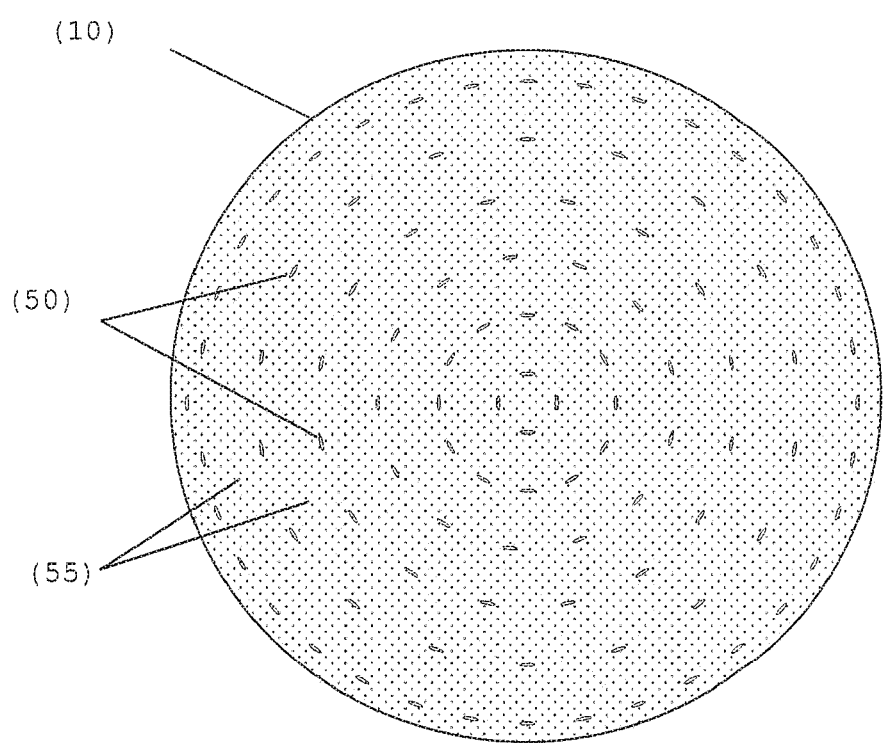
FIG. 6 is a top view of a circular polymer film having multiple load distribution elements of multiple sizes.

FIG. 6 depicts a perforated radially expanded polymer film (10) in which different types of load distribution elements (50) are present. Some of the load distribution elements (50) in FIG. 6 are an array of circumferentially oriented slits. In addition, FIG. 6 depicts an additional set of load distribution elements (50) such as a uniform pattern of smaller perforations (55). Any combination of shapes and/or patterns of load distribution elements may be used in the present invention provided that the load distribution elements can deform under an applied tensile load and yield an increase in load to failure compared to the polymer film having no load distribution elements.

When the present invention is applied to a surgical patch or surgical polymer film mesh made from a microporous fluoropolymer or microporous biocompatible polymer, a second material may be imbibed into microstructure to impart additional functionality. In this instance, the article would comprise both macroscopic load distribution elements and microporous elements. Materials such as but not limited to a hydrogel may be imbibed into the microporous elements to enhance cell ingrowth. Optionally, a second material may be coated onto the external surface of the micro porous material or applied to the internal surfaces of the microstructure of the microporous material. Coating materials such as, but not limited to, antibiotic or antiseptic materials may be useful to resist infection. The coating material, rheology, and process parameters can be adjusted to control the amount of material that is deposited on the available internal and/or external polymer film mesh surfaces. A broad range of complementary materials may be carried by or included in the present invention to meet the needs of numerous end applications.

Repairing damaged or weakened body tissues requires a relatively strong polymer film mesh having multiple load distribution elements. For example with a ventral hernia repair, the present invention can provide a 15 cm by 19 cm elliptical polymer film mesh having a Mesh Tension greater than 32 N/cm and yet be thin enough to be rolled up for delivery through a 5 mm trocar port. In the case of this 32 N/cm polymer film mesh, the thickness was about 0.01 cm. When an adhesion barrier is desired, a thinner polymer film mesh may be employed having a Mesh Tension greater than 16 N/cm. In which case, an even larger polymer film mesh will fit within the same 5 mm delivery trocar port. Alternatively a similar size polymer film mesh (elliptical shape measuring 15 cm×19 cm) could be packaged into a trocar having a diameter less than 5 mm. A 4 mm OD trocar may be used. Or a 3 mm OD trocar may be used.

The packaged polymer film mesh comprising at least one load distribution element may be sterilized while in a containment housing, or prior to insertion into the containment housing, or after relocation to the surgical device. Any suitable sterilization means may be used, including but not limited toy-radiation, steam, ethylene oxide {EtO), and peroxide.

In some surgical procedures, a different size or diameter delivery device may be warranted. The design parameters, including the number, size, shape, and location of load distribution element(s), may be changed accordingly. If the sole purpose is as an adhesion barrier, then a strength less than 16 N/cm may be useful in which case fewer load distribution elements may be necessary for a given polymer film thickness or a thinner film thickness could be used with equal or more load distribution elements. Alternatively, to meet small package size and high load requirements, the number, shape, and pattern of load distribution elements can be varied along with base polymer film properties.

Test Methods

Mesh Tension

Mesh Tensions for the examples described below were measured in accordance with ASTM D3787 based on the measured force and the radius of contact ($r_{contact}$) with the ball.

Mesh Tension=Force/$2_{TT}*r_{contact}$

The radius of contact ($r_{contact}$) was determined using contact paper as follows:

A nip impression kit (1 0002002 Nip Impression Kit from Metso Paper, P.O. Box 155, Ivy Industrial Park, Clarks Summit, Pa. 18411)) is used to measure the length of ball contact with the polymer film mesh. This kit contains a roll of carbon paper and a roll of plain white paper, which can be dispensed so that any given length of both will be obtained with the carbon side flush against the white paper. The two papers are inserted between the ball and the polymer film mesh. As the load or pressure is applied between the ball and the polymer film mesh the carbon paper will leave an ink mark impression in the shape of the knit on the white paper. The impression length on the white paper is measured with a steel ruler with 0.5 mm increments.

The length of ball contact and the radius of the ball are used to determine the angle of contact as shown in FIG. 6.

$2y$=length of ball contact/$r_{ball}$ $\square$=(length of ball contact/$r_{ball}$)/2

$r_{contact}=r_{ball}*\sin(\square)$ where, $2\square$=angle of contact
$r_{ball}$=radius of the ball
$r_{contact}$=radius of contact Suture Retention Suture retention is a mechanical property reflecting the articles mechanical resistance under tension at a suture site placed in the article. To represent the load applied by a suture at a suture site, a small pin fixture was used in which a pin (typically 0.020", or multiple pins) was pressed through a 1 inch wide strip of the test article. The coupon/attached-pin-fixture combination is attached in a tensile test apparatus such as an Instron Tensile Tester. The crosshead speed was set to 200 mm/min. For purposes of this measure, the maximum force exhibited was as the 'suture retention' strength. However, other parameters shown in the stress-strain graphs in FIGS. 6 and 7 may also be used to define the reinforcement phenomenon described herein.

The following nonlimiting examples are provided to further illustrate the present invention.

EXAMPLES

Tape 1

Fine powder of PTFE polymer as described and taught in U.S. Pat. No. 6,541,589, comprising perfluorobutylethylene modifier, was blended with Isopar K (Exxon Mobil Corp., Fairfax, Va.) in the 3 5 proportion of 0.200 gig of fine powder. The lubricated powder was compressed in a cylinder to form a pellet and placed into an oven set at 70° C. for approximately 8 hours. The compressed and heated pellet was ram extruded to produce an extrudate tape approximately 15.2 cm wide by 0.75 mm thick. The tape was then calendered between compression rolls, distended, and dried to yield a tape having matrix tensile strengths of 6 kpsi (machine direction}×6 kpsi (transverse direction}. The side of the resultant asymmetric polymer film mesh surface corresponding to Tape 1 is herein considered the tight-structure side.

Tape 2

Fine powder of PTFE polymer (DuPont, Wilmington, Del.) was blended with Isopar K (Exxon Mobil Corp., Fairfax, Va.) in the proportion of 0.243 g/g of fine powder. The lubricated powder was compressed in a cylinder to form a pellet. The compressed pellet was ram extruded at room temperature to produce an extrudate tape approximately 15.2 cm wide by 0.75 mm thick. The tape was then calendered between compression rolls, set to a temperature of 38° C., to a thickness of 0.28 mm. The tape was then longitudinally distended 8% and dried. The process produced a calendered tape having matrix tensile strengths of 3.2 kpsi (machine direction)×1.4 kpsi (transverse direction). The side of 15 the resultant asymmetric polymer film mesh surface corresponding to Tape 2 is herein considered the open-structure side.

Example 1

Thin Two-Sided Polymer Film Patch

Six layers of Tape 1 were stacked on top of one another, each layer being 90 degrees offset from the previous. The stack was compressed and laminated together under high vacuum (<29"Hg) at 309° C. and 100 k-lbs force for 4 minutes to full density on OEM press Model VAC-Q-LAM-1n5/14×13/2/4.0"/E370C/N/N/N-C-480V (OEM Press Systems Inc., 311 S. Highland Ave., Fullerton, Calif. 92832). The compressed stack was allowed to cool and then cut into an 8.5 inch diameter circle.

The circular sample was gripped around the periphery and radially expanded at 300° C. and an axial expansion rate of 3.0 inch/second to an area expansion of about 11.25:1. The radially expanded sample was then relaxed to achieve a 1.5:1 area reduction. The sample was removed and cut into a 9"×9" coupon. This process was repeated four times to create four radially expanded PTFE disks.

A polymer film mesh was created by combining four radially expanded PTFE disks from above with one layer of Tape 2 into a single stacked coupon. The stacked coupon was compressed and laminated together under high vacuum (<29"Hg) at 309° C. and—100 k-lbs force for 4 minutes to approximately full density on OEM press Model VAC-Q-LAM-1/75/14×13/2/4. O"/E370C/N/N/N-C-480V (OEM Press Systems Inc., 311 S. Highland Ave., Fullerton, Calif. 92832). The compressed densified stack was allowed to cool and cut to an 8.5 inch circle. The circular sample was gripped around the periphery and expanded at 300° C. and a rate of 0.2 inch/second axial displacement to an expansion ratio of about 11.25:1. The expanded polymer film mesh was then allowed to relax to an area reduction of about 1.5:1. The polymer film mesh was then restrained in a convection oven (ESPEC Model SSPH-201, 4141 Central Parkway, Hudsonville, Mich. 49426) at 350° C. for 10 minutes, and then allowed to cool.

A cross-sectional SEM of this microporous expanded asymmetric PTFE polymer film mesh article is shown in FIG. 5.

Example 2

Thin Two-Sided Polymer Film Patch Pre-Sutured with Suture Management

A sample of the polymer film mesh from Example 1 was cut into 15 cm×19 cm oval device using C02 Plotter/Laser (Universal Laser Systems Model PLS6.60-50 16000 M 81st Street, Scottsdale, Ariz. 85260). Then GORE-TEX CV-2 sutures (W. L. Gore and Associates, Inc., 301 Airport Road, Elkton, Md. 21921} were looped through at four cardinal locations: 12, 3, 6, and 9 o'clock positions. Each suture was passed about 0.5 cm inward from the edge. Each suture was looped through the device such that the free ends were on the abdominal side of the device. The entry and exit point of each suture loop was about 0.5 2 5 cm apart. Next a thin, strong piece of a fluorinated ethylene propylene (FEP)/expanded PTFE (ePTFE) composite film was cut into an approximately 1 cm×0.5 cm rectangle. The expanded PTFE film was prepared in conformance with U.S. Pat. No. 5,476,589A. The FEP layer was approximately 1 mil thick. This cut rectangle was placed on the open side of the sutured polymer film mesh so that each exposed suture was covered. These FEP/ePTFE rectangles where then welded to the polymer film mesh thereby securing the sutures in place. The welding was accomplished using a soldering gun with a blunt tip and set to 800° F. and hand pressure (Weller-WSD161, APEX Tool Group LLC., 14600 York Road Suite A, Sparks, Md. 21152).

Suture Management designed to avoid suture entanglement was accomplished by bundling attached pairs of oriented sutures using coils produced from a "string" of bioabsorbable polymer produced in conformance with U.S. Pat. No. 6,165,217. The bioabsorbable film mass was 7 mg/cm2. This film was "cigarette rolled" to produce the "string". This "string" was then looped around sutures securing the parallel adjacent sutures. Heat (260° F., 10 seconds) was applied via heat gun (Steinel Model HL2010E, 9051 Lyndale Avenue, Bloomington, Minn. 55420) to retract and thermally set the bioabsorbable polymer.

Example 3

Thin Two-Sided Polymer Film Patch Pre-Sutured Packed in Tube for Delivery Through 5 mm Trocar Port The sutured polymer film mesh article from Example 2 was folded in half across the ellipse minor axis. The folded polymer film mesh was placed between two small mandrels (or a split mandrel) (New England Precision Grinding, 0.013"×70" PTFE coated 304SS mandrels, 35 Jeffrey Avenue, Holliston, Mass. 01746-2027) that were chucked on a horizontal rotary drill press and the drill press rotated to roll up sutured polymer film mesh device into a tight package around the mandrels. The rolled assembly was removed from the chucks, and the mandrels removed from within the rolled, sutured polymer film mesh. The rolled, sutured polymer film mesh was inserted into a −5.2 mm I D tube (nylon tubing of 0.005" wall from Grilamid). The tube and rolled suture device was inserted into a 5 mm trocar port of ID −5.5 mm (Covidien 15 Hampshire Street, Mansfield, Mass. 02048). Deployment of the sutured polymer film mesh was demonstrated when the rolled sutured polymer film mesh was easily pushed out of the trocar and unrolled onto the table top where is laid relatively flat.

Example 4

Load Distribution

5:1 Elliptical Aperture

Figure 7:
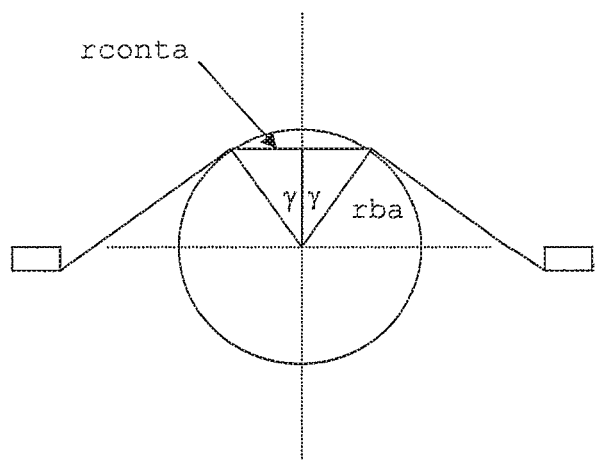
FIG. 7 is a schematic depicting how the radius of contact was determined in the Mesh Tension test method.

The suture retention effect of creating elliptical apertures was determined using an ePTFE polymer film mesh article created in 30 conformance with U.S. Pat. No. 7,306,729. The base ePTFE material had matrix tensile strengths of 48 kpsi and 46 kpsi in the machine and transverse directions, respectively. The material was mounted in a C02 plotter/laser (Universal Laser Systems Model PLS6.60-50 16000 M 81$^{st}$ Street, Scottsdale, Ariz. 85260). The beam was focused on the plane of the material. In the orientation of the test directions (machine direction, transverse direction, and 45 degree nominally), an ellipse having $r_{major}$ 0.05" and $r_{minor}$ 0.010" (i.e. 5:1 ratio) was laser cut from the material oriented so the ellipse was substantially parallel to the perimeter of the polymer film mesh article. The suture retention measurements were performed by sequentially locating the test pin in a lased aperture in each of the machine, transverse, and 45 degree directions. The results are shown in FIG. 7.

Example 5

Load Distribution

2:1 Elliptical Aperture

The suture retention effect of creating elliptical apertures was determined using an ePTFE polymer film mesh article created in conformance with U.S. Pat. No. 7,306,729. The base ePTFE material had matrix tensile strengths of 48 kpsi and 46 kpsi in the machine and transverse directions, respectively. The material was mounted in a C02 plotter/laser (Universal Laser Systems Model PLS6.60-50 16000 M 81$^{st}$ Street, Scottsdale, Ariz. 85260). The beam was focused on the plane of the material. In the orientation of the test directions (machine direction, transverse direction, and 45 degree nominally), an ellipse having $r_{major}$ 0.05" and $r_{minor}$ 0.025" (i.e. 5:1 ratio) was laser cut from the material oriented so the ellipse was substantially parallel to the perimeter of the polymer film mesh article. The suture retention measurements were performed by sequentially locating the test pin in a lased aperture in each of the machine, transverse, and 45 degree directions. The results are shown in FIG. 7.

Example 6

Load Distribution

1:1 Elliptical Aperture

The suture retention effect of creating elliptical apertures was determined using an ePTFE polymer film mesh article created in conformance with U.S. Pat. No. 7,306,729. The base ePTFE material had matrix tensile strengths of 48 kpsi and 46 kpsi in the machine and transverse directions, respectively. The material was mounted in a C02 plotter/laser (Universal Laser Systems Model PLS6.60-50 16000 M 81$^{st}$ Street, Scottsdale, Ariz. 85260). The beam was focused on the plane of the material. In the orientation of the test directions (machine direction, transverse direction, and 45 degree nominally), an ellipse having $r_{major}$ 0.05" and $r_{minor}$ 0.050" (i.e. 5:1 ratio) was laser cut from the material oriented so the ellipse was substantially parallel to the perimeter of the polymer film mesh article. The suture retention measurements were performed by sequentially locating the test pin in a lased aperture in each of the machine, transverse, and 45 degree directions. The results are shown in FIG. 7.

Example 7

Load Distribution

Control, No Elliptical Aperture

The suture retention effect of creating elliptical apertures was determined using an ePTFE polymer film mesh article created in conformance with U.S. Pat. No. 7,306,729. The base ePTFE material had matrix tensile strengths of 48 kpsi and 46 kpsi in the machine and transverse directions, respectively. This control sample was tested by pressing the test pin through the polymer film mesh article in locations corresponding to each of the machine, transverse, and 45 degree directions. The results are shown in FIG. 7.

Example 8

Load Distribution

Slit Element

Figure 8:
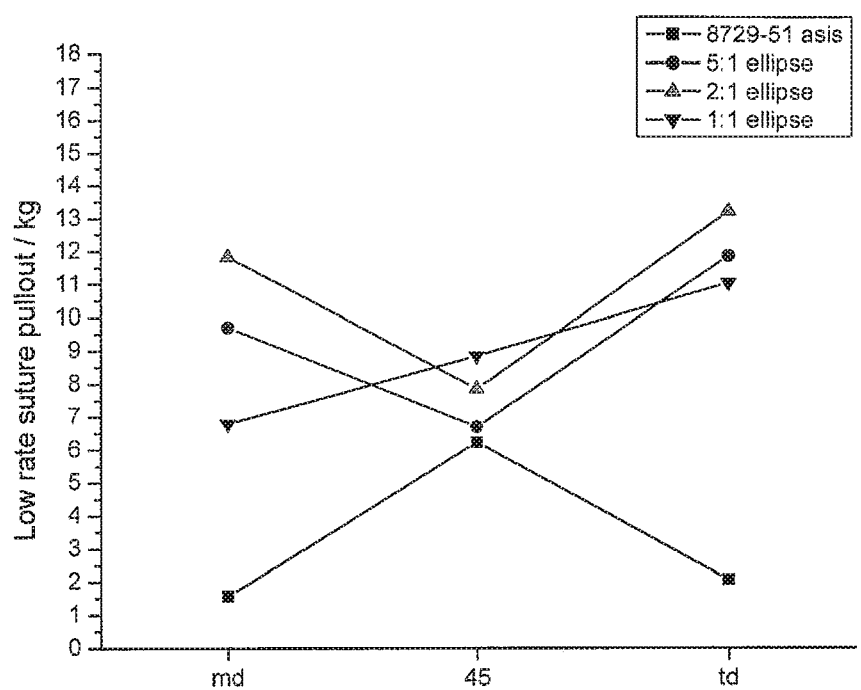
FIG. 8 is a graph of polymer film mesh orientation angle and suture pull-out force as a function of elliptical aperture aspect ratio.
Figure 9:
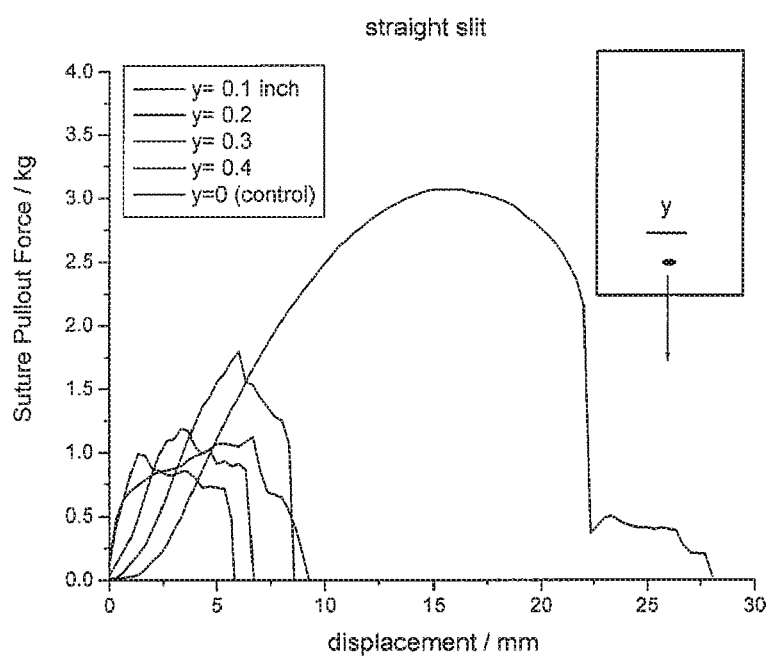
FIG. 9 is a graph of tensile test displacement versus suture pullout as a function of slit width.
Figure 10:
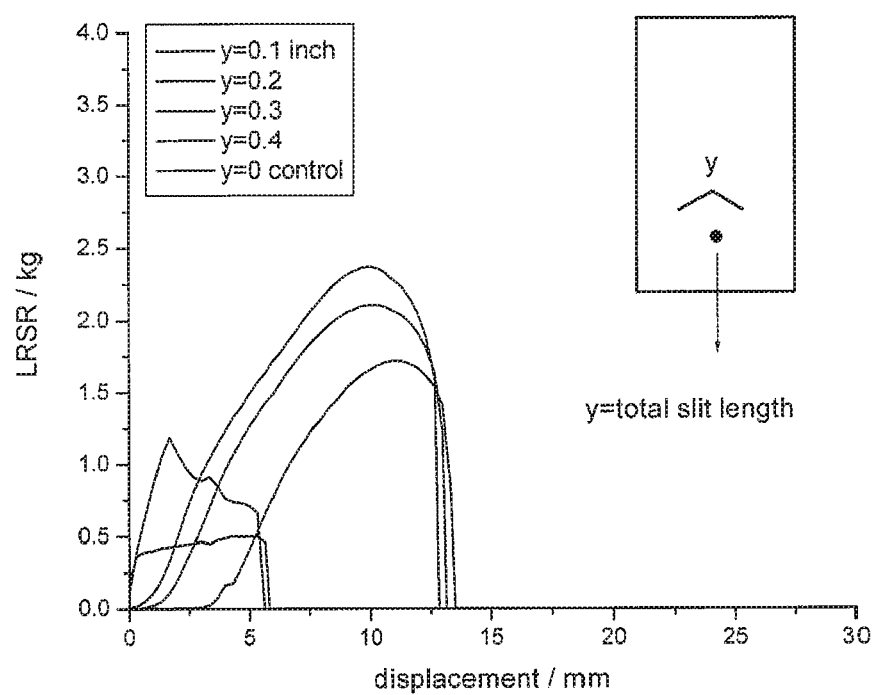
FIG. 10 is a graph of tensile test displacement versus suture pull-out as a function of "hat" shaped slit width.

The effect on suture retention of creating a small slit near the suture location determined using an ePTFE polymer film mesh article created in conformance with U.S. Pat. No. 7,306,729. The base ePTFE material had matrix tensile strengths of 48 kpsi and 46 kpsi in the machine and transverse directions, respectively. A small slit cut was cut with a razor blade approximately 0.5 cm in from and parallel to the edge of the polymer film mesh article. The test pin was then pressed through the polymer film mesh article at a location between the slit and the edge of the article. The tensile properties were measured. FIG. 8 shows the suture pull-out tensile results as a function of slit length compared to a control sample having no slit.

Example 9

Load Distribution

"Hat" Element

The effect on suture retention of creating a small "hat" shaped slit near the suture location determined using an ePTFE polymer film mesh article created in conformance with U.S. Pat. No. 7,306,729. The base ePTFE material had matrix tensile strengths of 48 kpsi and 46 kpsi in the machine and transverse directions, respectively. A small "hat" shaped slit cut was cut with a razor blade approximately 0.5 em in from and parallel to the edge of the polymer film mesh article. The test pin was then pressed through the polymer film mesh article at a location between the "hat" shaped slit and the edge of the article. The tensile properties were measured. FIG. 8 shows the suture pull-out tensile results as a function of the "hat" shaped slit length compared to a control sample having no slit.

Example 10

Multiple Longitudinal Load Distribution Elements

Tear Resistance in the machine direction of a material comprising multiple load distribution elements was evaluated as follows: An ePTFE article was created based on U.S. Pat. No. 7,306,729 resulting in material of average mass of 193 g/m2, an average density of 2.1 g/cc, and an MTS (MD) 36 kpsi & (TD) 55 kpsi. The material was mounted in a C02 plotter/laser (Universal Laser Systems Model PLS6.60-50 16000 M 81$^{st}$ Street, Scottsdale, Ariz. 85260). The beam was focused on the plane of the material. A matrix of ellipses of $r_{major}$ 0.02" and $r_{minor}$ 0.004" were lased into the continuous material. The ellipses were oriented with the minor-axis parallel to the machine direction of the material. The ellipses were longitudinally spaced apart 0.07" (nominal center-on-center), and 0.08" transversely (nominal edge-to-edge). The resulting material had a hole pattern as depicted by the uniform pattern of smaller perforations (55) in FIG. 6.

Figure 11:
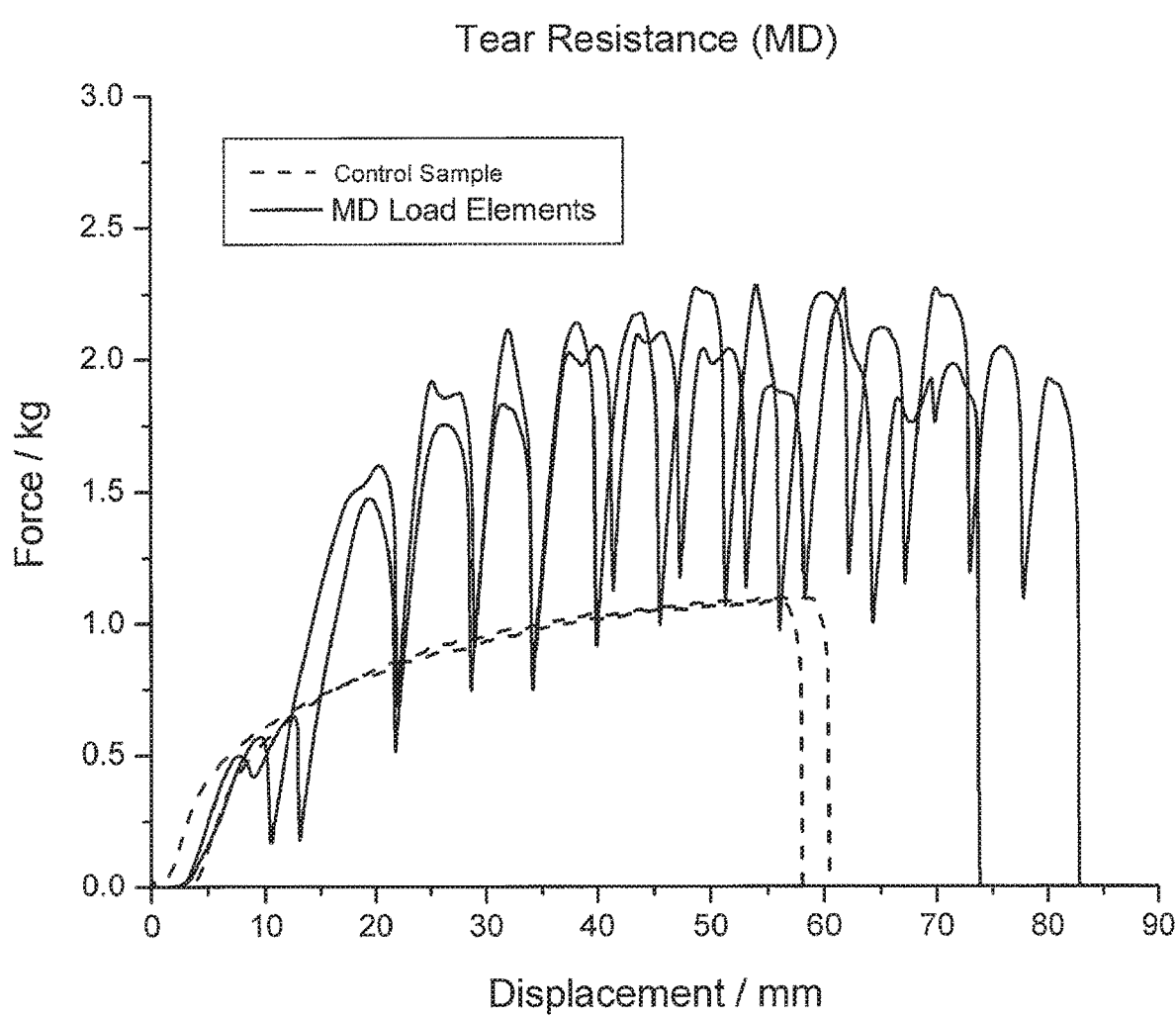
FIG. 11 is a graph of tear propagation results in the machine, longitudinal direction for a mesh having multiple load distribution means.

A 1 inch by 2 inch sample test coupon was cut and removed from both the as received material as well as material with the lased matrix of load distribution elements described in above in this Example. The tear propagation characteristics of each sample were tested substantially in accordance with ASTM D1938 Trouser Tear Method. The sample test coupon long axis was oriented parallel to the machine direction of the material. A sharp tear was initiated by manually slitting the coupon along the long axis using a sharp razor blade. Each tab was mounted in the lower and upper grips in a tensile tester, and tested at 200 mm/min cross head speed and the resultant force trace was recorded. The Force versus Displacement data for both the control and lased samples are depicted in FIG. 11. The maximum force held by the lased samples is significantly higher than that for the control sample. This proves that with respect to maximum force or load bearing capacity, cutting a multitude of 3 o holes in this thin film specimen increased machine direction tensile properties by approximately two times.

Example 11

Multiple Transverse Load Distribution Elements

Tear Resistance in the transverse direction of a material comprising multiple load distribution elements was evaluated as follows: An ePTFE article was created based on U.S. Pat. No. 7,306,729 resulting in material of average mass of 193 g/m2, an average density of 2.1 g/cc, and an MTS (MD) 36 kpsi & (TD) 55 kpsi. The material was mounted in a C02 plotter/laser (Universal Laser Systems Model PLS6.60-50 16000 M 81$^{st}$ Street, Scottsdale, Ariz. 85260). The beam was focused on the plane of the material. A matrix of ellipses of r major 0.02" and r minor 0.004" were lased into the continuous material. The ellipses were oriented with s the minor-axis parallel to the transverse direction of the material. The ellipses were longitudinally spaced apart 0.07" (nominal center-on-enter), and 0.08" transversely (nominal edge-to-edge). The resulting material had a hole pattern as depicted by the uniform pattern of smaller perforations (55) in FIG. 6.

Figure 12:
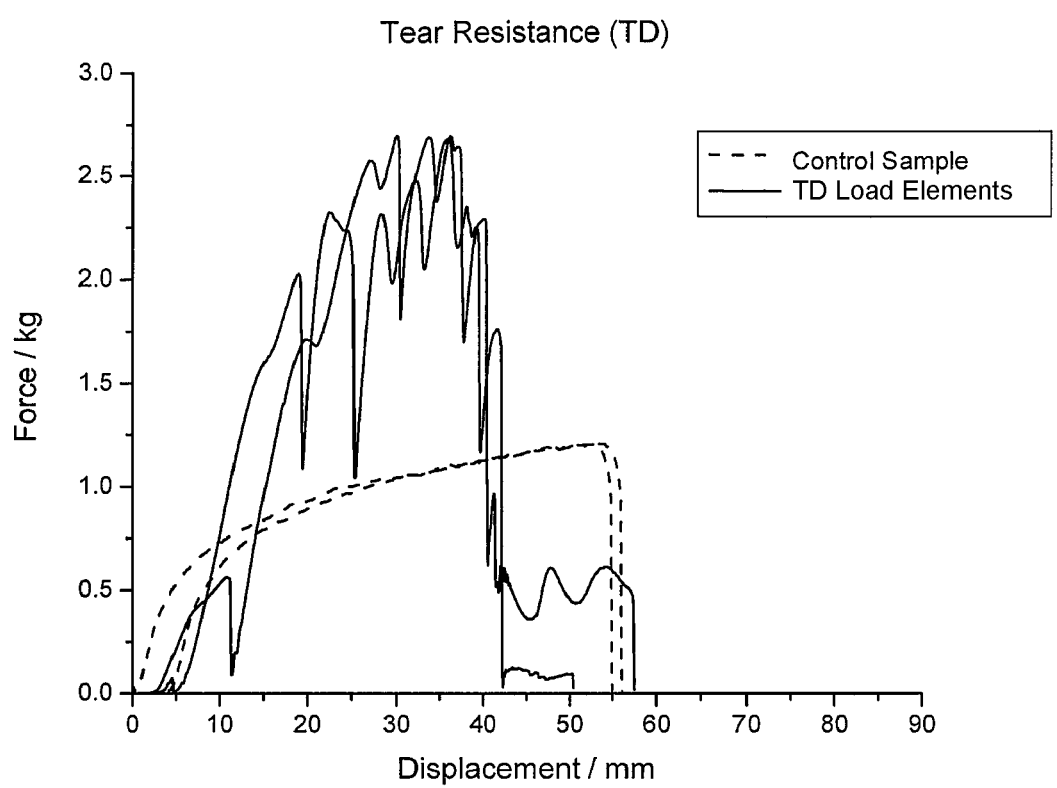
FIG. 12 is a graph of tear propagation results in the transverse direction for a mesh having multiple load distribution means.

A 1 inch by 2 inch sample test coupon was cut and removed from both the as received material as well as material with the lased matrix of load distribution elements described above in this Example. The tear propagation characteristics of each sample were tested substantially in accordance with ASTM 01938 Trouser Tear Method. The sample test coupon long axis was oriented parallel to the transverse direction of the material. A sharp tear was initiated by manually slitting the coupon along the long axis using a sharp razor blade. Each tab was mounted in the lower and upper grips in a tensile tester, and tested at 200 mm/min crosshead speed and the resultant force trace was recorded. The Force versus Displacement data for both the control and lased samples are depicted in FIG. 12. The maximum force held by the lased samples is significantly higher than that for the control sample. This proves that with respect to maximum force or load bearing capacity, cutting a multitude of holes in this thin film specimen increased transverse direction tensile 2 5 properties by approximately two times.

What is claimed is:

1. A method for increasing the load required for failure of a polymer film, the method comprising:
   creating a first series of macroscopic load distribution elements in a polymer film that is microporous and that has undergone in plane radial expansion, the first series of load distribution elements oriented circumferentially around the polymer film;
   creating a second series of macroscopic load distribution elements that are smaller than the first series of load distribution elements in the polymer film, the second series of load distribution elements oriented concentrically with respect to the first series of load distribution elements;
   attaching a tether to the polymer film proximate to at least one load distribution element of the first series of load distribution elements, wherein a width of the at least one load distribution element in a lateral dimension is oriented transverse to a longitudinal length of the tether, the lateral dimension defining a first direction and a second opposing direction; and
   applying a tensile load to the polymer film via the tether such that the tensile load is applied to the polymer film along an interface width, the interface width being oriented transverse to the applied tensile load, wherein the width of the at least one load distribution element exceeds the interface width such that the at least one load distribution element extends further along each of the first and second directions of the lateral dimension than does the interface width, and
   wherein the at least one of the first series of load distribution elements deforms under applied tensile load and yields an increase in the load required for failure compared to the polymer film prior to the creation of the at least one of the first series of load distribution elements.

2. The method of claim 1,
   wherein attaching the tether to the polymer film proximate to at least one of the first series of load distribution elements comprises attaching the tether to the polymer film proximate to each of the first series of load distribution elements.

3. The method of claim 1, wherein the at least one of the first series of load distribution elements comprises at least one of a group consisting of:
   a slit; and
   a load distribution perforation.

4. The method of claim 1, wherein the polymer film has a thickness selected from a group consisting of:
   a thickness less than 0.10 inch;
   a thickness less than 0.050 inch;

a thickness less than 0.010 inch; and
a thickness less than 0.002 inch.

5. The method of claim 1, wherein the at least one of the first series of load distribution elements has a width greater than a width of the tether.

6. The method of claim 1,
wherein the tether is attached to the polymer film via at least one attachment element, and
wherein the at least one of the first series of load distribution elements has a width greater than a width of the attachment element.

7. The method of claim 6, wherein the attachment element includes one or more of a group consisting of:
an adhesive;
a mechanical interlock;
a sewn connection;
a suture; and
a staple.

8. The method of claim 1, wherein the polymer film is a surgical polymer film.

9. The method of claim 1, further comprising:
creating the first series of load distribution elements in the polymer film, wherein the first series of load distribution elements includes the at least one of the first series of load distribution elements;
attaching, to each of the first series of load distribution elements in the polymer film, at least one of a plurality of tethers, wherein the plurality of tethers includes the tether,
wherein the polymer film further includes, in addition to the first series of load distribution elements, a plurality of perforations forming a uniform pattern, and each of the plurality of perforations forming the uniform pattern are smaller than each of the first series of load distribution elements, and
wherein the plurality of perforations forming the uniform pattern are each smaller than widths of the plurality of tethers.

10. The method of claim 1, further comprising creating a third series of load distribution elements oriented concentrically with respect to the second series of load distribution elements.

11. The method of claim 10, further comprising attaching at least one tether to the polymer film proximate to each of the third series of load distribution elements.

12. An assembly comprising:
a polymer film that is microporous and that has undergone in plane radial expansion;
wherein the polymer film includes a first series of load distribution elements, the first series of load distribution elements oriented circumferentially around the polymer film;
a second series of load distribution elements that are smaller than the first series of load distribution elements in the polymer film, the second series of load distribution elements oriented concentrically with respect to the first series of load distribution elements; and
at least one tether attached to the polymer film proximate to each of the first series of load distribution elements to define an interface width along which the at least one tether is adapted to transfer a force to the polymer film,
wherein for each of the first series of load distribution elements:
a width of the load distribution element in a lateral dimension is oriented transverse to a longitudinal length of a corresponding one of the at least one tethers, the lateral dimension defining a first direction and a second opposing direction, and the interface width being oriented transverse to the longitudinal length of the corresponding tether,
wherein the width of the load distribution element exceeds the interface width such that the load distribution element extends further along each of the first and second directions of the lateral dimension than does the interface width, and
wherein each of the first series of load distribution elements deforms under applied tensile load and yields an increase in the load required for failure compared to the polymer film prior to the creation of the first series of load distribution elements.

13. The assembly of claim 12,
wherein the first series of load distribution elements includes a plurality of circumferentially oriented load distribution elements,
wherein at least one tether includes at least one tether attached to the polymer film proximate to each of the first series of load distribution elements.

14. The assembly of claim 12, wherein the first series of load distribution elements comprises at least one of a group consisting of:
a slit; and
a load distribution perforation.

15. The assembly of claim 12, wherein the polymer film has a thickness selected from a group consisting of:
a thickness less than 0.10 inch;
a thickness less than 0.050 inch;
a thickness less than 0.010 inch; and
a thickness less than 0.002 inch.

16. The assembly of claim 12, wherein each of the first series of load distribution elements has a width greater than a width of the at least one tether.

17. The assembly of claim 12,
wherein the at least one tether is attached to the polymer film via at least one attachment element, and
wherein each of the first series of load distribution elements has a width greater than a width of the attachment element.

18. The assembly of claim 17, wherein the attachment element includes one or more of a group consisting of:
an adhesive;
a mechanical interlock;
a sewn connection;
a suture; and
a staple.

19. The assembly of claim 12, wherein the polymer film is a surgical polymer film.

20. The assembly of claim 12, further comprising:
a plurality of tethers including the at least one tether; and
wherein at least one of the plurality of tethers is attached to each of the first series of load distribution elements in the polymer film,
wherein the polymer film further includes, in addition to the first series of load distribution elements, a plurality of perforations forming a uniform pattern, and each of the plurality of perforations forming the uniform pattern are smaller than each of the first series of load distribution elements, and
wherein the plurality of perforations forming the uniform pattern are each smaller than widths of the plurality of tethers.

21. The assembly of claim 12, further comprising a third series of load distribution elements oriented concentrically with respect to the second series of load distribution elements.

22. The assembly of claim 21, wherein at least one tether includes at least one tether attached to the polymer film proximate each of the third series of load distribution elements.

\* \* \* \* \*